(12) United States Patent
Mayer

(10) Patent No.: US 9,393,126 B2
(45) Date of Patent: Jul. 19, 2016

(54) BILATERALLY PLACED DISC PROSTHESIS FOR SPINAL IMPLANT AND METHOD OF BILATERAL PLACEMENT

(71) Applicant: Peter L. Mayer, Sarasota, FL (US)

(72) Inventor: Peter L. Mayer, Sarasota, FL (US)

(*) Notice: Subject to any disclaimer, the term of this patent is extended or adjusted under 35 U.S.C. 154(b) by 463 days.

(21) Appl. No.: 13/845,810

(22) Filed: Mar. 18, 2013

(65) Prior Publication Data

US 2013/0310936 A1  Nov. 21, 2013

Related U.S. Application Data

(60) Provisional application No. 61/636,230, filed on Apr. 20, 2012.

(51) Int. Cl.
*A61F 2/44* (2006.01)
*A61F 2/46* (2006.01)
*A61F 2/30* (2006.01)

(52) U.S. Cl.
CPC .............. *A61F 2/4425* (2013.01); *A61F 2/442* (2013.01); *A61F 2/4611* (2013.01); *A61F 2002/30235* (2013.01); *A61F 2002/30286* (2013.01); *A61F 2002/30405* (2013.01); *A61F 2002/30507* (2013.01); *A61F 2002/30579* (2013.01); *A61F 2002/30594* (2013.01); *A61F 2002/444* (2013.01); *A61F 2002/4629* (2013.01)

(58) Field of Classification Search
USPC ............................................ 623/17.11–17.16
See application file for complete search history.

(56) References Cited

U.S. PATENT DOCUMENTS

| | | | | |
|---|---|---|---|---|
| 725,874 | A | * | 4/1903 | Riley ............................ 269/48.1 |
| 2,485,531 | A | * | 10/1949 | Dzus ..................... A61B 17/683 |
| | | | | 606/104 |
| 3,986,383 | A | * | 10/1976 | Petteys ........................... 72/393 |
| 4,041,939 | A | | 8/1977 | Hall |
| 4,349,921 | A | | 9/1982 | Kuntz |

(Continued)

FOREIGN PATENT DOCUMENTS

| | | |
|---|---|---|
| DE | 4208116 | 9/1993 |
| EP | 0042271 | 12/1981 |

(Continued)

OTHER PUBLICATIONS

International Preliminary Report on Patentability and Written Opinion dated Mar. 22, 2011 for PCT/US2009/057369 filed Sep. 17, 2009.

(Continued)

*Primary Examiner* — Anu Ramana
*Assistant Examiner* — Jessica Weiss
(74) *Attorney, Agent, or Firm* — Fleit Gibbons Gutman Bongini & Bianco PL

(57) ABSTRACT

A spinal prosthesis for insertion bilaterally into an annulotomy hole created laterally in a spinal disc between two abutting vertebrae that is composed of a first elongated member having first threading at one end and an end cap at its other end, a second elongated member having an end cap with a threaded hole fixed to one end of a hollow tube open-ended at its other end. The members are telescoped together with the threading of the first member mated with the threaded hole of the second member and the open end of said hollow tube disengageably engaged with the end cap of the first member for rotation together. A method for bilaterally implanting the members of the prosthesis using a wire, and then telescopically mating them.

10 Claims, 27 Drawing Sheets

(56) References Cited

U.S. PATENT DOCUMENTS

| | | | |
|---|---|---|---|
| 4,465,220 A * | 8/1984 | Ledlow et al. | 228/50 |
| 4,772,287 A | 9/1988 | Ray et al. | |
| 4,863,476 A * | 9/1989 | Shepperd | 623/17.15 |
| 4,865,604 A * | 9/1989 | Rogozinski | 623/23.42 |
| 4,944,753 A | 7/1990 | Burgess | |
| 4,973,301 A * | 11/1990 | Nissenkorn | 604/8 |
| 5,047,055 A | 9/1991 | Bao et al. | |
| 5,059,193 A * | 10/1991 | Kuslich | 606/247 |
| 5,100,405 A * | 3/1992 | McLaren | A61B 17/72 |
| | | | 606/304 |
| 5,171,278 A * | 12/1992 | Pisharodi | 128/898 |
| 5,298,254 A | 3/1994 | Prewett | |
| 5,390,683 A * | 2/1995 | Pisharodi | 128/898 |
| 5,454,365 A * | 10/1995 | Bonutti | 600/204 |
| 5,456,667 A * | 10/1995 | Ham et al. | 604/107 |
| 5,514,180 A | 5/1996 | Heggeness | |
| 5,545,229 A | 8/1996 | Parsons et al. | |
| 5,562,735 A | 10/1996 | Margulies | |
| 5,571,189 A | 11/1996 | Kuslich | |
| 5,653,763 A * | 8/1997 | Errico et al. | 623/17.11 |
| 5,662,657 A | 9/1997 | Carn | |
| 5,693,100 A * | 12/1997 | Pisharodi | 623/17.16 |
| 5,865,846 A | 2/1999 | Bryan | |
| 5,919,194 A * | 7/1999 | Anderson | 606/313 |
| 5,951,553 A | 9/1999 | Betz | |
| 5,964,807 A | 10/1999 | Chin Chin Gan | |
| 6,048,342 A | 4/2000 | Zucherman | |
| 6,063,121 A | 5/2000 | Xavier et al. | |
| 6,093,205 A | 7/2000 | McLeod et al. | |
| 6,110,210 A | 8/2000 | Norton et al. | |
| 6,126,688 A | 10/2000 | McDonnell | |
| 6,146,420 A | 11/2000 | McKay | |
| 6,146,422 A | 11/2000 | Lawson | |
| 6,214,012 B1 | 4/2001 | Karpman | |
| 6,224,600 B1 * | 5/2001 | Protogirou | 606/63 |
| 6,240,926 B1 | 6/2001 | Chin Chin Gan | |
| 6,264,695 B1 | 7/2001 | Stoy | |
| 6,287,308 B1 | 9/2001 | Betz | |
| 6,319,255 B1 * | 11/2001 | Grundei et al. | 606/76 |
| 6,368,319 B1 | 4/2002 | Schaefer | |
| 6,395,034 B1 | 5/2002 | Suddaby | |
| 6,419,704 B1 | 7/2002 | Ferree | |
| 6,419,706 B1 | 7/2002 | Graf | |
| 6,451,020 B1 | 9/2002 | Zucherman et al. | |
| 6,451,057 B1 * | 9/2002 | Chen et al. | 623/17.15 |
| 6,494,883 B1 * | 12/2002 | Ferree | A61F 2/28 |
| | | | 606/247 |
| 6,500,178 B2 | 12/2002 | Zucherman et al. | |
| 6,500,182 B2 * | 12/2002 | Foster | 606/127 |
| 6,500,206 B1 | 12/2002 | Bryan | |
| 6,554,833 B2 * | 4/2003 | Levy et al. | 606/63 |
| 6,582,467 B1 * | 6/2003 | Teitelbaum et al. | 623/17.11 |
| 6,632,224 B2 | 10/2003 | Cachia | |
| 6,676,665 B2 * | 1/2004 | Foley et al. | 606/105 |
| 6,733,531 B1 | 5/2004 | Trieu | |
| 6,780,175 B1 * | 8/2004 | Sachdeva et al. | 604/531 |
| 6,821,298 B1 * | 11/2004 | Jackson | 623/17.15 |
| 6,929,640 B1 | 8/2005 | Underwood | |
| 6,966,930 B2 * | 11/2005 | Arnin et al. | 623/17.11 |
| 6,974,479 B2 | 12/2005 | Trien | |
| 6,997,929 B2 | 2/2006 | Manzi | |
| 7,001,431 B2 | 2/2006 | Bao et al. | |
| 7,004,971 B2 | 2/2006 | Serhan | |
| 7,048,764 B2 | 5/2006 | Ferree | |
| 7,101,400 B2 | 9/2006 | Thramann | |
| 7,153,305 B2 | 12/2006 | Johnson | |
| 7,204,853 B2 | 4/2007 | Gordon | |
| 7,238,206 B2 | 7/2007 | Lange | |
| 7,250,060 B2 | 7/2007 | Trieu | |
| 7,261,738 B2 | 8/2007 | Casey | |
| 7,270,682 B2 | 9/2007 | Frigg et al. | |
| 7,371,238 B2 | 5/2008 | Soboleski | |
| 7,452,369 B2 * | 11/2008 | Barry | 606/279 |
| 7,491,236 B2 * | 2/2009 | Cragg | A61B 17/70 |
| | | | 606/301 |
| 7,569,055 B2 * | 8/2009 | Zander | A61B 17/725 |
| | | | 606/64 |
| 7,601,152 B2 * | 10/2009 | Levy et al. | 606/63 |
| 7,621,950 B1 * | 11/2009 | Globerman et al. | 623/17.11 |
| 7,758,644 B2 * | 7/2010 | Trieu | 623/17.11 |
| 7,763,074 B2 * | 7/2010 | Altarac et al. | 623/17.11 |
| 7,799,056 B2 | 9/2010 | Sankaran | 606/246 |
| 7,799,081 B2 | 9/2010 | McKinley | 623/17.16 |
| 7,824,429 B2 | 11/2010 | Culbert | A61B 17/7064 |
| | | | 606/279 |
| 7,959,652 B2 * | 6/2011 | Zucherman et al. | 606/249 |
| 8,092,459 B2 * | 1/2012 | Malandain | 606/86 A |
| 8,096,994 B2 * | 1/2012 | Phan et al. | 606/86 A |
| 8,097,018 B2 * | 1/2012 | Malandain et al. | 606/246 |
| 8,100,943 B2 * | 1/2012 | Malandain et al. | 606/246 |
| 8,105,358 B2 * | 1/2012 | Phan | 606/249 |
| 8,187,333 B2 | 5/2012 | Mayer | |
| 8,241,335 B2 * | 8/2012 | Truckai et al. | 606/279 |
| 8,262,736 B2 * | 9/2012 | Michelson | A61F 2/446 |
| | | | 623/17.16 |
| 8,323,344 B2 * | 12/2012 | Galley et al. | 623/17.16 |
| 8,409,282 B2 * | 4/2013 | Kim | 623/17.11 |
| 8,512,407 B2 * | 8/2013 | Butler et al. | 623/17.16 |
| 8,518,115 B2 * | 8/2013 | Chavatte et al. | 623/17.12 |
| 8,529,628 B2 * | 9/2013 | Marino et al. | 623/17.16 |
| 8,556,949 B2 * | 10/2013 | Teisen et al. | 606/327 |
| 8,641,769 B2 * | 2/2014 | Malandain | 623/17.16 |
| 8,784,491 B2 * | 7/2014 | Biedermann et al. | 623/17.11 |
| 8,814,908 B2 * | 8/2014 | Druma et al. | 606/248 |
| 8,821,497 B2 * | 9/2014 | Stupak | A61B 17/842 |
| | | | 606/300 |
| 8,906,022 B2 * | 12/2014 | Krinke et al. | 606/63 |
| 8,940,048 B2 * | 1/2015 | Butler et al. | 623/17.15 |
| 8,961,518 B2 * | 2/2015 | Taylor et al. | 606/79 |
| 8,986,386 B2 * | 3/2015 | Oglaza et al. | 623/17.15 |
| 9,039,742 B2 * | 5/2015 | Altarac et al. | 606/249 |
| 2002/0022887 A1 * | 2/2002 | Huene | 623/17.16 |
| 2002/0120334 A1 | 8/2002 | Crozet | |
| 2002/0183848 A1 | 12/2002 | Ray et al. | |
| 2003/0176921 A1 | 9/2003 | Lawson | |
| 2003/0181979 A1 * | 9/2003 | Ferree | 623/17.11 |
| 2003/0204260 A1 | 10/2003 | Ferree | |
| 2004/0010317 A1 | 1/2004 | Lambrechi et al. | |
| 2004/0097927 A1 * | 5/2004 | Yeung et al. | 606/61 |
| 2004/0133204 A1 * | 7/2004 | Davies | 606/63 |
| 2004/0204763 A1 * | 10/2004 | Ralph et al. | 623/17.13 |
| 2004/0258732 A1 | 12/2004 | Shikinami | |
| 2004/0260297 A1 | 12/2004 | Padget | |
| 2005/0015150 A1 | 1/2005 | Lee | |
| 2005/0015152 A1 | 1/2005 | Sweeney | |
| 2005/0113919 A1 | 5/2005 | Cragg et al. | |
| 2005/0113923 A1 | 5/2005 | Acker et al. | |
| 2005/0113929 A1 | 5/2005 | Cragg | |
| 2005/0143827 A1 * | 6/2005 | Globerman et al. | 623/17.16 |
| 2005/0182414 A1 | 8/2005 | Manzi | |
| 2005/0187559 A1 | 8/2005 | Raymond | |
| 2005/0222681 A1 * | 10/2005 | Richley et al. | 623/17.11 |
| 2005/0234557 A1 * | 10/2005 | Lambrecht et al. | 623/17.16 |
| 2005/0261781 A1 * | 11/2005 | Sennett et al. | 623/23.54 |
| 2005/0273166 A1 * | 12/2005 | Sweeney | 623/17.11 |
| 2005/0278028 A1 * | 12/2005 | Mujwid | 623/17.13 |
| 2005/0278036 A1 * | 12/2005 | Leonard et al. | 623/23.47 |
| 2006/0136061 A1 | 6/2006 | Navarro et al. | |
| 2006/0161166 A1 | 7/2006 | Johnson | |
| 2006/0235417 A1 * | 10/2006 | Sala | 606/79 |
| 2006/0235534 A1 | 10/2006 | Gertzman et al. | |
| 2006/0253132 A1 | 11/2006 | Evans | |
| 2006/0253198 A1 | 11/2006 | Myint et al. | |
| 2006/0271061 A1 * | 11/2006 | Beyar et al. | 606/105 |
| 2006/0276790 A1 * | 12/2006 | Dawson et al. | 606/61 |
| 2006/0276897 A1 | 12/2006 | Winslow et al. | |
| 2006/0276901 A1 | 12/2006 | Zipnick et al. | |
| 2006/0276902 A1 | 12/2006 | Zipnick et al. | |
| 2006/0287730 A1 | 12/2006 | Segal et al. | |
| 2007/0010889 A1 | 1/2007 | Francis | |
| 2007/0027546 A1 | 2/2007 | Palm et al. | |
| 2007/0038222 A1 | 2/2007 | Bhatnagar et al. | |
| 2007/0038301 A1 | 2/2007 | Hudgins | |
| 2007/0043440 A1 * | 2/2007 | William et al. | 623/17.11 |

(56) References Cited

U.S. PATENT DOCUMENTS

| | | | |
|---|---|---|---|
| 2007/0050037 A1 | 3/2007 | Snell et al. | |
| 2007/0061012 A1 | 3/2007 | Cauthen, III | |
| 2007/0067034 A1* | 3/2007 | Chirico et al. | 623/17.11 |
| 2007/0067039 A1 | 3/2007 | Lambrecht et al. | |
| 2007/0073402 A1 | 3/2007 | Vresilovic et al. | |
| 2007/0088436 A1* | 4/2007 | Parsons et al. | 623/17.11 |
| 2007/0173826 A1* | 7/2007 | Canaveral et al. | 606/61 |
| 2007/0173939 A1* | 7/2007 | Kim et al. | 623/17.11 |
| 2007/0179612 A1 | 8/2007 | Johnson | |
| 2007/0219634 A1* | 9/2007 | Greenhalgh et al. | 623/17.16 |
| 2007/0239280 A1 | 10/2007 | Keith | |
| 2008/0009875 A1* | 1/2008 | Sankaran et al. | 606/84 |
| 2008/0039944 A1* | 2/2008 | Malandain et al. | 623/17.16 |
| 2008/0051893 A1* | 2/2008 | Malandain et al. | 623/17.11 |
| 2008/0051894 A1* | 2/2008 | Malandain et al. | 623/17.11 |
| 2008/0051895 A1* | 2/2008 | Malandain et al. | 623/17.11 |
| 2008/0058934 A1* | 3/2008 | Malandain et al. | 623/17.11 |
| 2008/0071356 A1* | 3/2008 | Greenhalgh et al. | 623/1.16 |
| 2008/0183204 A1* | 7/2008 | Greenhalgh et al. | 606/198 |
| 2008/0221624 A1* | 9/2008 | Gooch | 606/302 |
| 2008/0262617 A1* | 10/2008 | Froehlich et al. | 623/14.12 |
| 2008/0281346 A1* | 11/2008 | Greenhalgh et al. | 606/191 |
| 2008/0281364 A1* | 11/2008 | Chirico et al. | 606/86 A |
| 2009/0005821 A1* | 1/2009 | Chirico et al. | 606/319 |
| 2009/0012564 A1* | 1/2009 | Chirico et al. | 606/246 |
| 2009/0024157 A1* | 1/2009 | Anukhin | 606/200 |
| 2009/0054935 A1* | 2/2009 | Miller et al. | 606/86 R |
| 2009/0204216 A1* | 8/2009 | Biedermann et al. | 623/17.12 |
| 2009/0292323 A1* | 11/2009 | Chirico et al. | 606/86 R |
| 2010/0070035 A1* | 3/2010 | Mayer | A61F 2/442 623/17.16 |
| 2010/0185287 A1* | 7/2010 | Allard et al. | 623/17.11 |
| 2010/0185291 A1* | 7/2010 | Jimenez et al. | 623/17.16 |
| 2010/0217325 A1* | 8/2010 | Hochschuler et al. | 606/264 |
| 2010/0228301 A1* | 9/2010 | Greenhalgh et al. | 606/313 |
| 2011/0029082 A1* | 2/2011 | Hall | 623/17.11 |
| 2011/0230965 A1* | 9/2011 | Schell | A61B 17/1757 623/17.11 |
| 2011/0270396 A1* | 11/2011 | Leibowitz | 623/17.11 |
| 2012/0004732 A1* | 1/2012 | Goel et al. | 623/17.16 |
| 2012/0046748 A1* | 2/2012 | Weiman | 623/17.16 |
| 2012/0265304 A1* | 10/2012 | Mayer | 623/17.12 |
| 2013/0158669 A1* | 6/2013 | Sungarian et al. | 623/17.16 |
| 2013/0190877 A1* | 7/2013 | Medina | 623/17.16 |
| 2013/0197642 A1* | 8/2013 | Ernst | 623/17.16 |
| 2013/0197647 A1* | 8/2013 | Wolters et al. | 623/17.16 |
| 2013/0226251 A1* | 8/2013 | Chegini et al. | 606/325 |
| 2013/0310883 A1* | 11/2013 | Levy et al. | 606/313 |
| 2013/0310936 A1* | 11/2013 | Mayer | 623/17.15 |
| 2013/0317617 A1* | 11/2013 | Mayer | 623/17.16 |
| 2014/0012336 A1* | 1/2014 | Biedermann et al. | 606/313 |
| 2014/0031940 A1* | 1/2014 | Banouskou | 623/17.16 |
| 2014/0121775 A1* | 5/2014 | Hardenbrook et al. | 623/17.16 |
| 2014/0243982 A1* | 8/2014 | Miller | 623/17.16 |
| 2014/0257484 A1* | 9/2014 | Flower et al. | 623/17.15 |
| 2014/0350608 A1* | 11/2014 | Goel et al. | 606/279 |
| 2015/0012098 A1* | 1/2015 | Eastlack et al. | 623/17.15 |

FOREIGN PATENT DOCUMENTS

| | | | |
|---|---|---|---|
| FR | 2639823 | 6/1990 | |
| FR | 2723841 | 3/1996 | |
| FR | 2772594 | 6/1999 | |
| FR | 2862866 | 6/2005 | |
| WO | 0013620 | 3/2000 | |
| WO | 0013691 | 3/2000 | |
| WO | 2004064692 | 8/2004 | |
| WO | 2004089240 | 10/2004 | |
| WO | 2005084589 | 9/2005 | |
| WO | 2006078663 | 7/2006 | |
| WO | 2007048252 | 5/2007 | |
| WO | WO 2011/048140 A1 * | 4/2011 | A61B 17/88 |

OTHER PUBLICATIONS

International Search Report dated May 4, 2010 for PCT/US2009/057369 filed Sep. 17, 2009.

* cited by examiner

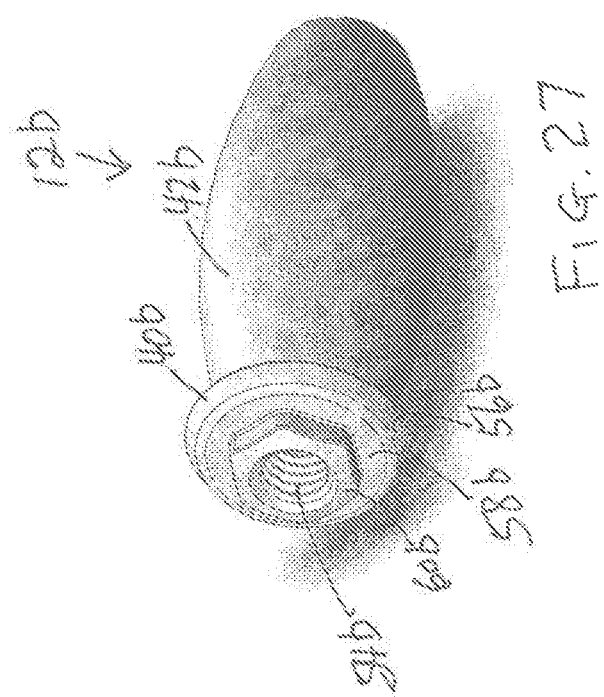

US 9,393,126 B2

BILATERALLY PLACED DISC PROSTHESIS FOR SPINAL IMPLANT AND METHOD OF BILATERAL PLACEMENT

CROSS REFERENCE TO RELATED APPLICATION

This invention relates to a disc prosthesis for spinal implant as shown and described in related application U.S. Provisional Patent Application Ser. No. 61/636,230 filed Apr. 19, 2012, the contents of which are here incorporated in their entirety. The benefits of 35 U.S.C, §120 are claimed.

BACKGROUND

Intervertebral discs (or more simply "discs") lie between adjacent vertebrae in the spine. Each disc forms a cartilaginous joint to allow slight movement of the vertebrae and acts as a ligament to hold the vertebrae together.

Discs include an outer annulus fibrosus, which surrounds the inner nucleus pulposus. The annulus fibrosus includes several layers of fibrocartilage. The nucleus pulposus contains loose fibers suspended in a mucoprotein gel, which has the consistency of semi-hard and slightly fibrous connective tissue or cartilage. The nucleus of the disc acts as a shock absorber for distributing pressure evenly across the disc and for absorbing the impact of bending and twisting of the spine while keeping the two abutting vertebrae separated. When one develops a prolapsed disc, the nucleus pulposus is forced out resulting in pressure being put on nerves located near the disc. This can cause severe pain and neurological problems. There is one disc between each pair of adjacent vertebrae, except between the first and second cervical vertebrae. The atlas is the first cervical (neck) vertebra which is just under the head. The axis is the second cervical vertebra. The axis acts as a post around which the atlas can rotate, allowing the neck to rotate. There are a total of twenty-three discs in the spine. The discs are most commonly identified by specifying the particular vertebrae they separate. For example, the disc between the fifth and sixth cervical vertebrae is designated "C5-6". As people age, intervertebral discs tend to degenerate. Two typical processes can occur. The nucleus pulposus dehydrates and flattens, which limits its ability to absorb shock. The annulus fibrosus gets weaker with age and develops fissures or tears. As the discs dehydrate, the disc spaces change and the space for adjacent nerves narrows. In the neural foramens, this is called foraminal stenosis; in the spinal canal, this is called central stenosis. The discs bulge outward, and bone spurs (osteophytes) form along the bulging disc surfaces that also pinch adjacent nerves (spinal cord, cauda equina, and nerve roots). A flattening disc causes stress to the posterior elements of the spine and also the facet joints. Although these conditions may not cause pain in some people, others experience acute and chronic pain. Pain, weakness, and numbness due to pinching of the nerves protruding from the spine are called radiculopathy or radiculitis. Pain, weakness, and numbness due to pinching of the nerves inside the spinal canal is known as radiculopathy, radiculitis, cauda equina syndrome or myelopathy, depending on the level of the spine and the type of symptoms. When the annulus fibrosus tears due to an injury or the degenerative process, the nucleus pulposus may begin to extrude through the tear. This is called disc herniation. Near the posterior aspect of each disc, at each vertebral level or segment, a pair of major spinal nerves extends outward, to different organs, tissues, extremities, etc. Herniated discs often press against these nerves (pinched nerve) and the spinal cord causing neurologic dysfunction including sensory and/or motor loss and/or pain. Herniated disc, ruptured disc, bulging disc, degenerative disc, protrusion, extrusion, all refer to related processes and are used more-or-less synonymously, depending on the medical professional. There is no true standard nomenclature, and the various terms mean different things to different people. Also, the degree to which there is pressure on the nerves (e.g. stenosis, pinching, nerve root elevation, cord compression, effacement, and many other descriptions) also varies. To treat impaired discs, many techniques and devices have been used. Some treatments remove, dissolve, or vaporize disc material (e.g. chymopapain injection, microsurgical discectomy, nucleotomy, laser discectomy, radiofrequency ablation, and others). Other treatments fuse the disc (e.g. cages, screws, bone grafts, bone morphogenic protein, and others). Disc removal procedures remove the disc. Fusion procedures result in loss of motion of the disc and juxtaposed vertebrae. Accordingly, there is a need for an implantable prosthesis that treats the conditions noted above in a more efficacious manner to restore to a damaged disc area the original natural body motion function.

SUMMARY OF THE INVENTION

This existing need is met by the implantable prosthesis of the present invention, which is bilaterally easily and quickly implantable by insertion into a damaged intervertebral disc.

A spinal prosthesis is provided for insertion bilaterally into an annulotomy hole created laterally in a spinal disc between two abutting vertebrae comprising a first elongated member having first threading at one end and an end cap at its other end, a second elongated member having an end cap with a threaded hole fixed to one end of a hollow tube open-ended at its other end. The members are telescoped together following separate bilateral implanting via a wire. The threading of said first member is mated with the threaded hole of said second member and the open end of said hollow tube is disengageably engaged with the end cap of said first member for rotation together. Also a method is provided for implanting a disc prosthesis in a disc space between two abutting vertebrae. The prosthesis is composed of two longitudinally divided components that telescope together. Each component consists of a main load-bearing body portion with an end cap. The method includes the steps of using a wire and dilators to form a tract in a disc space, separately bilaterally spinally implanting each component in the tract formed in the spinal disc, and then coupling the components together (via telescoping) between the two abutting vertebrae.

BRIEF DESCRIPTION OF THE DRAWINGS

FIG. 27 is another perspective view of the one member of the prosthesis shown in FIG. 25

DETAILED DESCRIPTION OF PREFERRED EMBODIMENTS OF THE INVENTION

Figure 1:
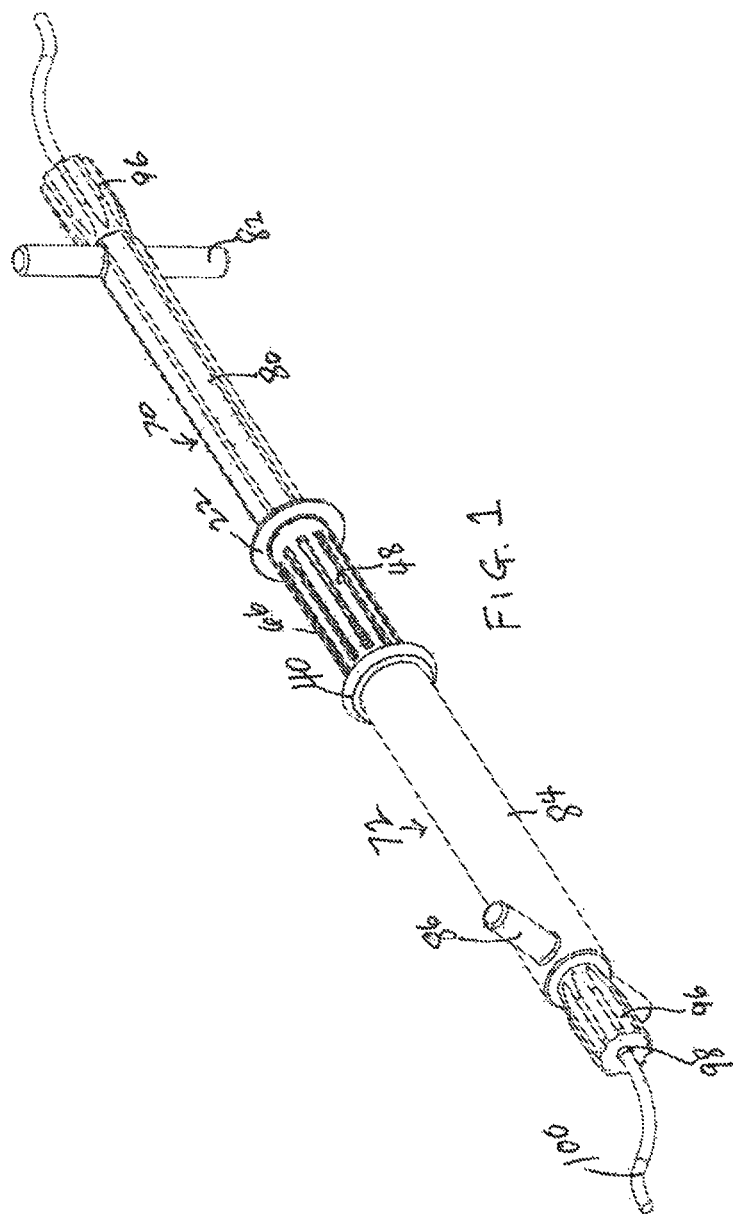
FIG. 1 is a perspective view of an expansible prosthesis with implanting tools coupled.
Figure 2:
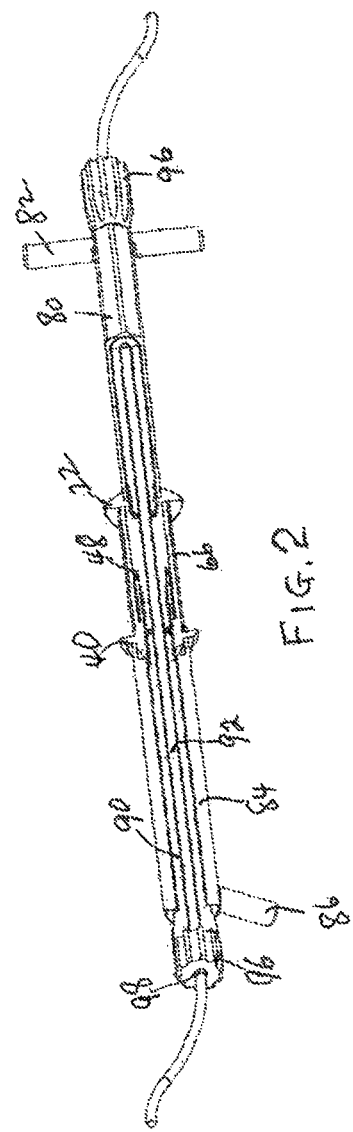
FIG. 2 is a sectional view taken through the mid-plane of the prosthesis of FIG. 1.
Figure 3:
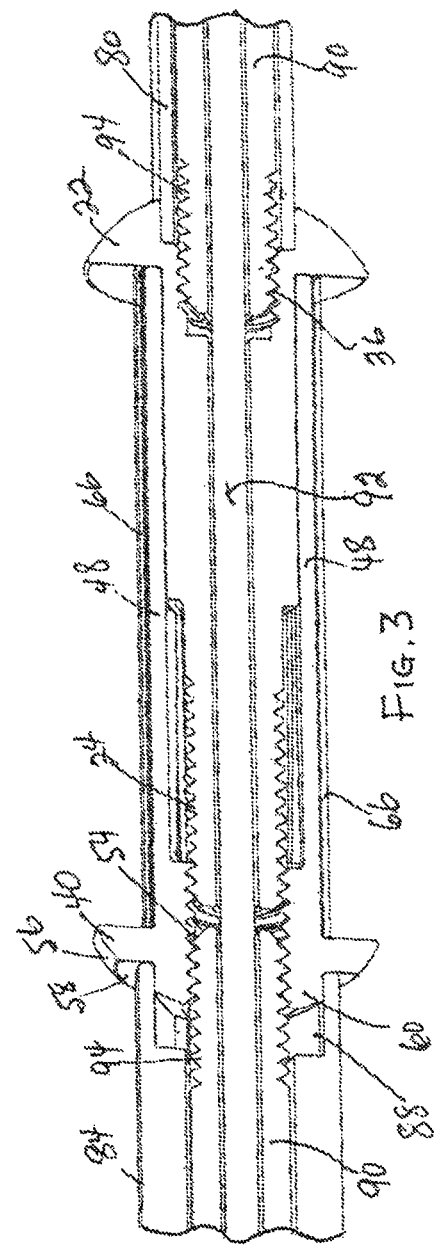
FIG. 3 is an enlarged sectional view of the central portion of FIG. 2.
Figure 4:
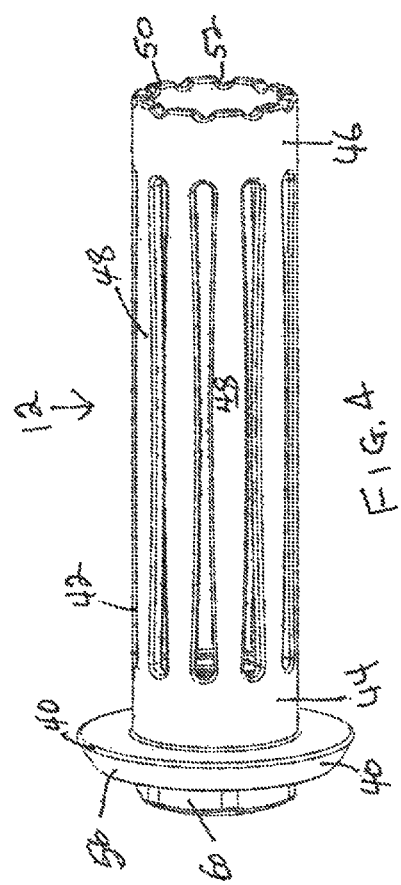
FIG. 4 is a perspective view of a member of the prosthesis.
Figure 5:
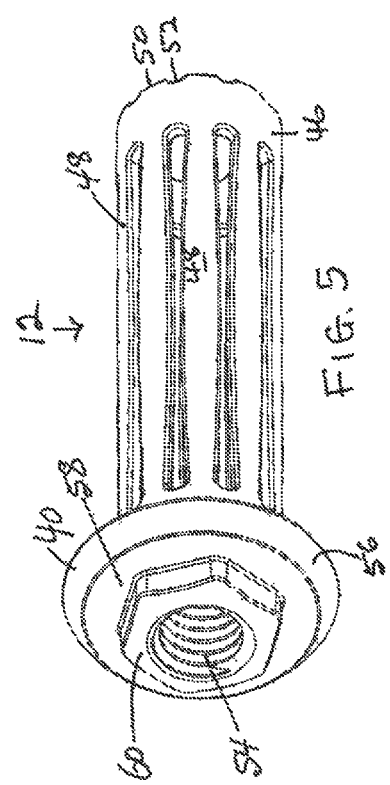
FIG. 5 is another perspective view of the member shown in FIG. 4.
Figure 6:
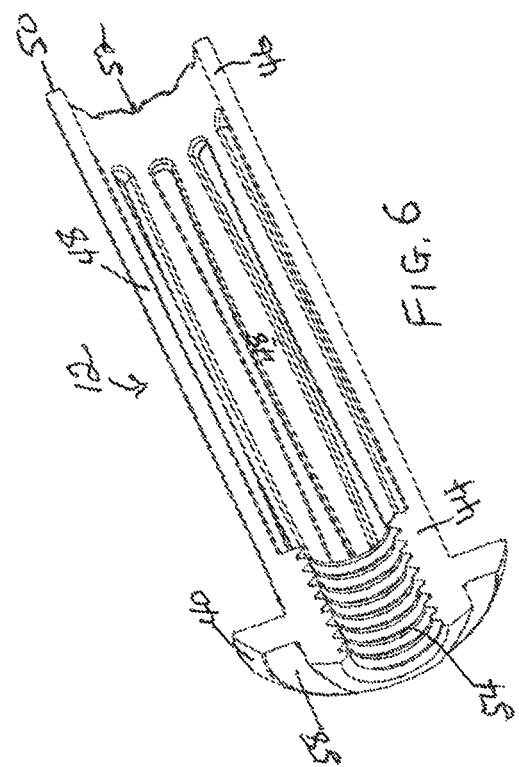
FIG. 6 is a sectional view of the member shown in FIG. 4 through its mid-plane.
Figure 7:
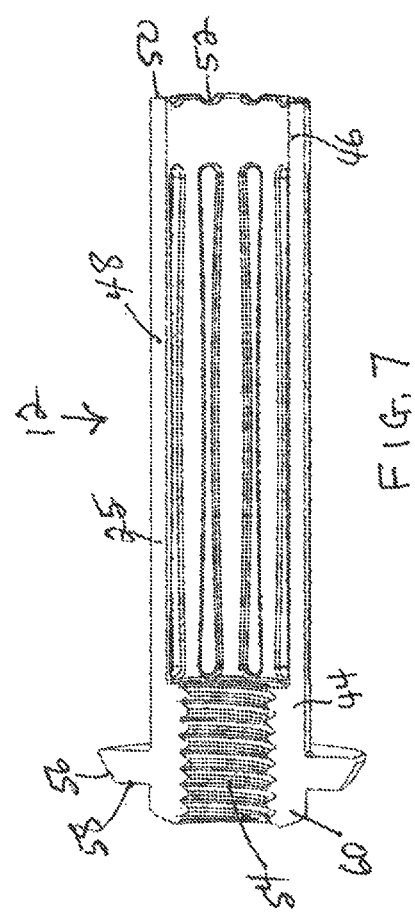
FIG. 7 is another sectional view of the member shown in FIG. 4 through its mid-plane.
Figure 8:
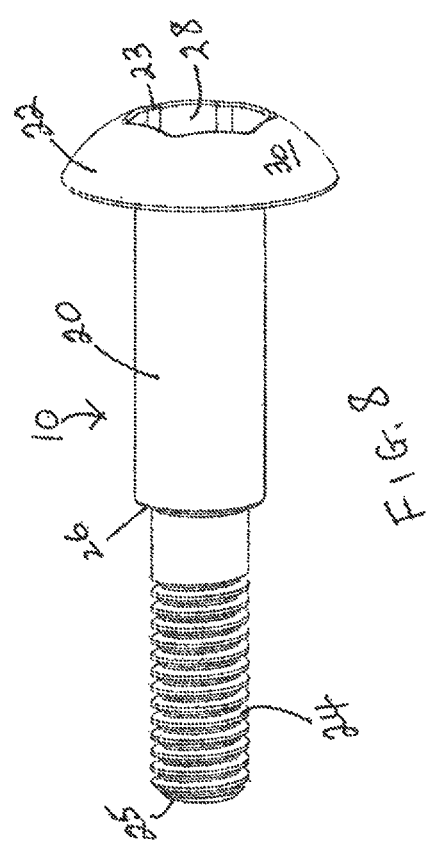
FIG. 8 is a perspective view of a second member of the prosthesis.
Figure 9:
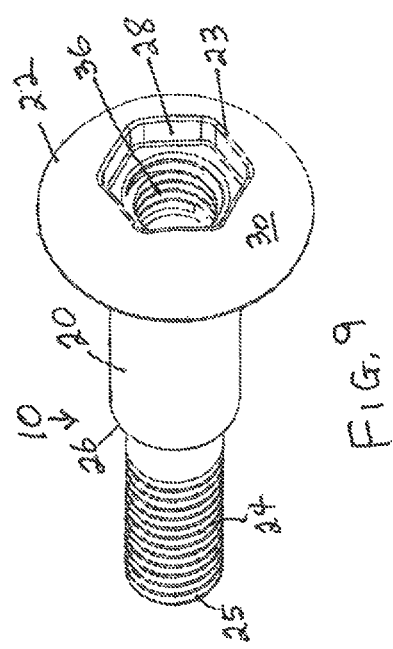
FIG. 9 is another perspective view of the second member shown in FIG. 8.
Figure 10:
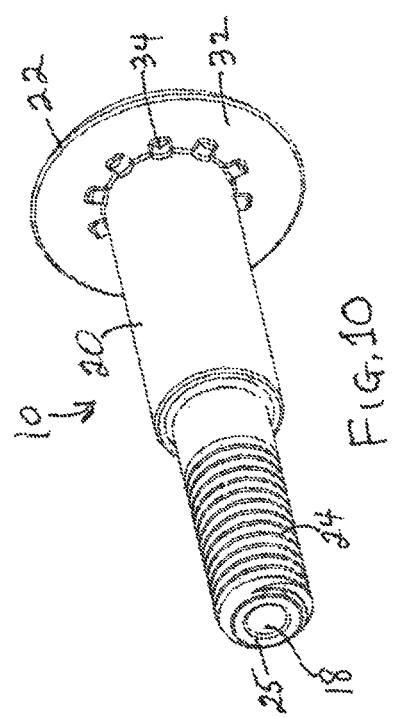
FIG. 10 is still another perspective view of the second member shown in FIG. 8.
Figure 17:
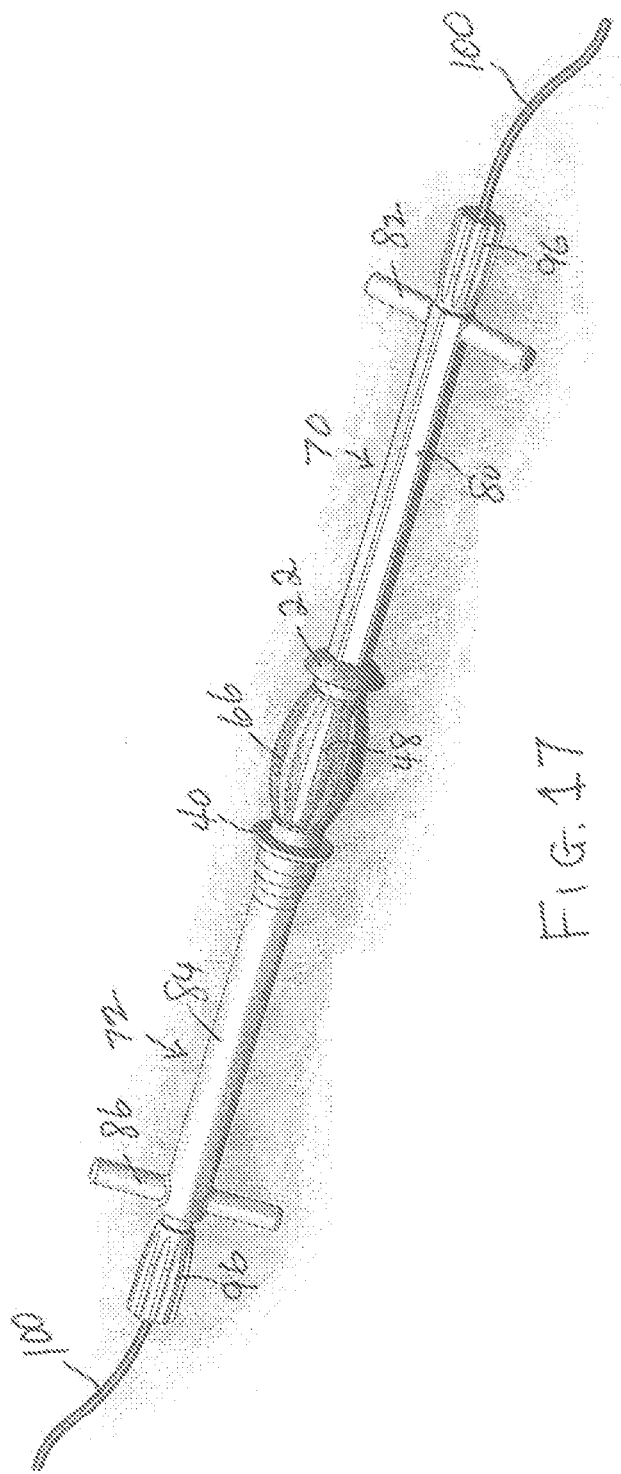
FIG. 17 is perspective view of an expansible prosthesis with tools coupled, the prosthesis having both proximal and distal flanged end caps.
Figure 18:
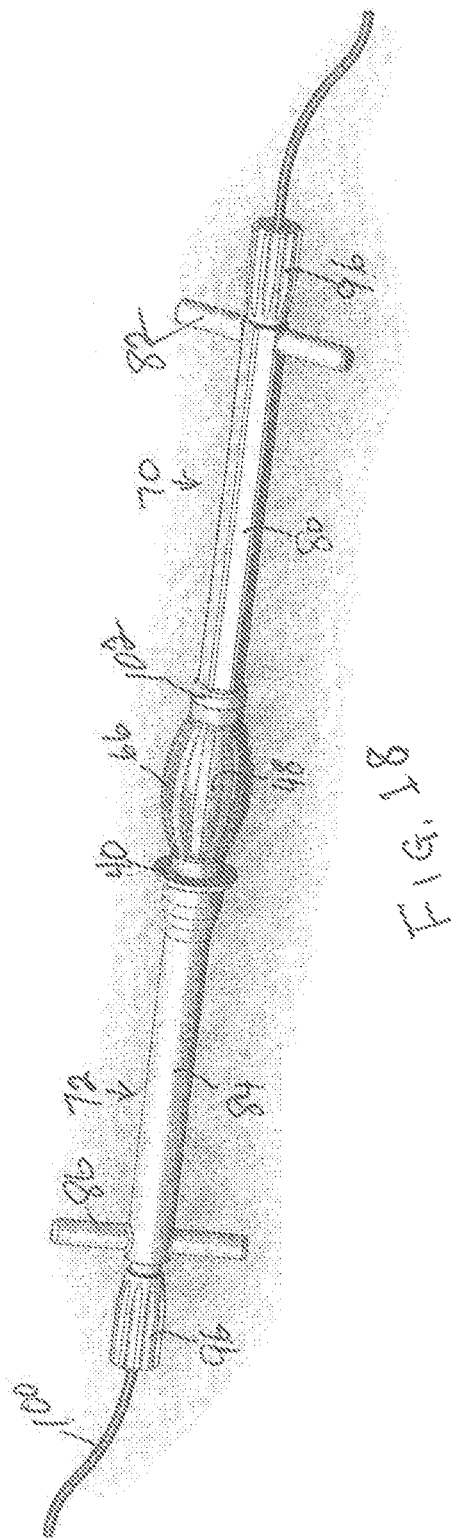
FIG. 18 is a perspective view like FIG. 17 showing the prosthesis using one end cap without a flange.
Figure 19:
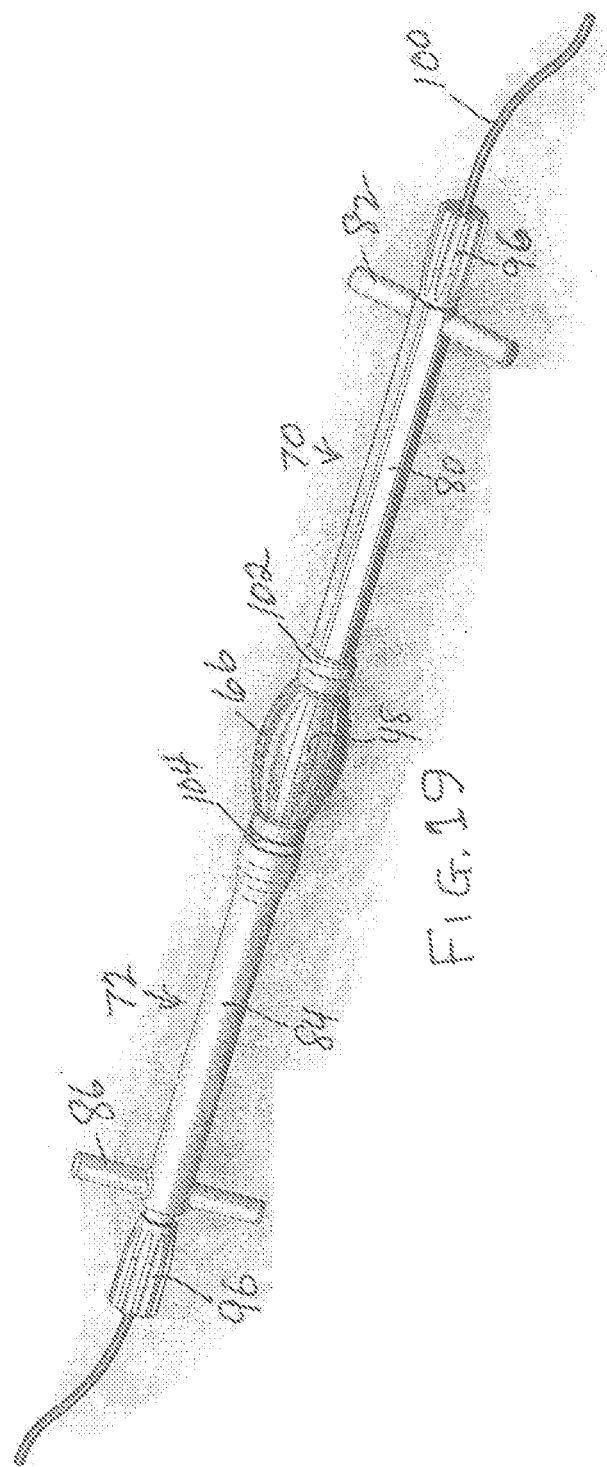
FIG. 19 is a perspective view like FIG. 17 showing the prosthesis using both end caps without flanges.
Figure 20:
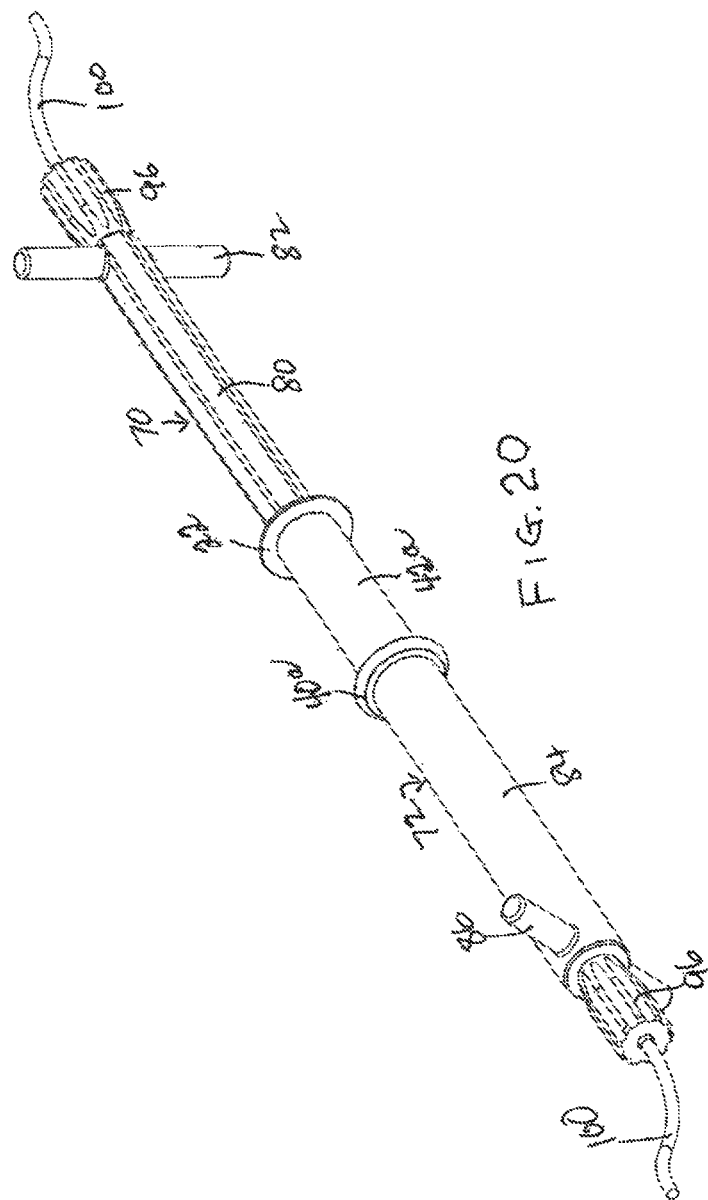
FIG. 20 is perspective view of a cylindrical prosthesis with tool coupled, the prosthesis having flanged end caps.
Figure 21:
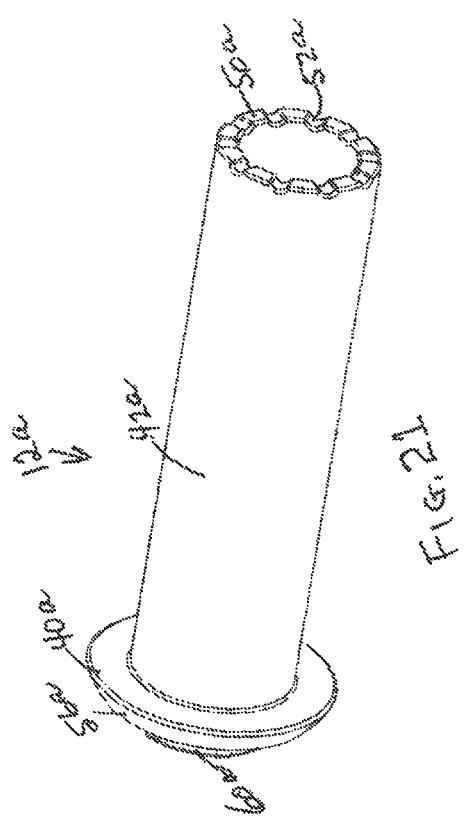
FIG. 21 is a perspective view of one member of the prosthesis shown in FIG. 20.
Figure 22:
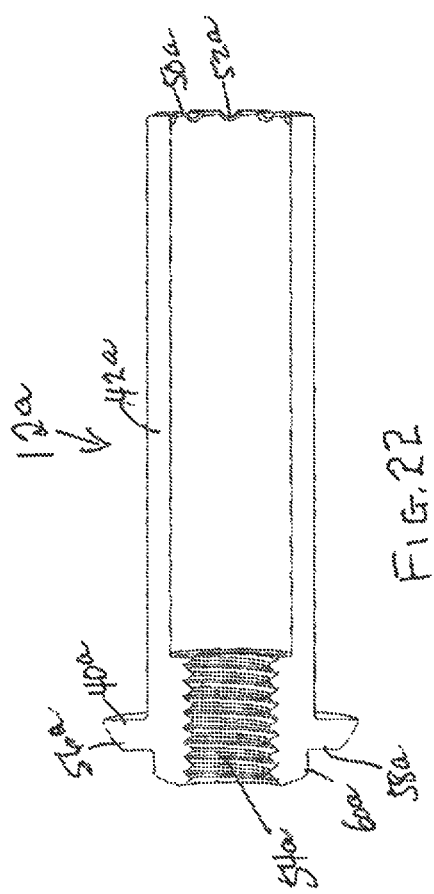
FIG. 22 is a sectional view of the member shown in FIG. 21 taken along the mid-plane.
Figure 23:
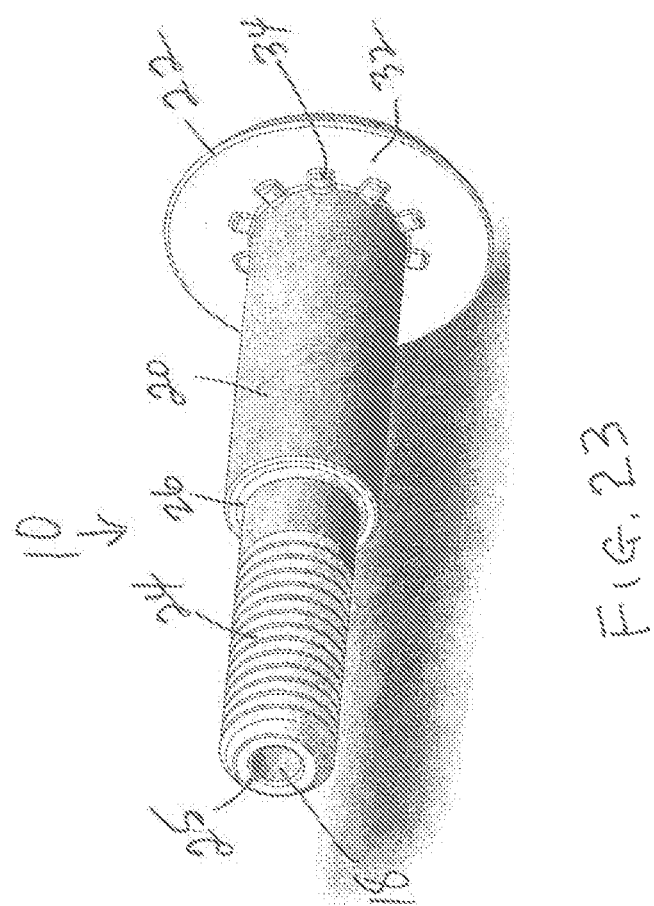
FIG. 23 is a perspective view of the other member of the prosthesis shown in FIG. 20.
Figure 24:
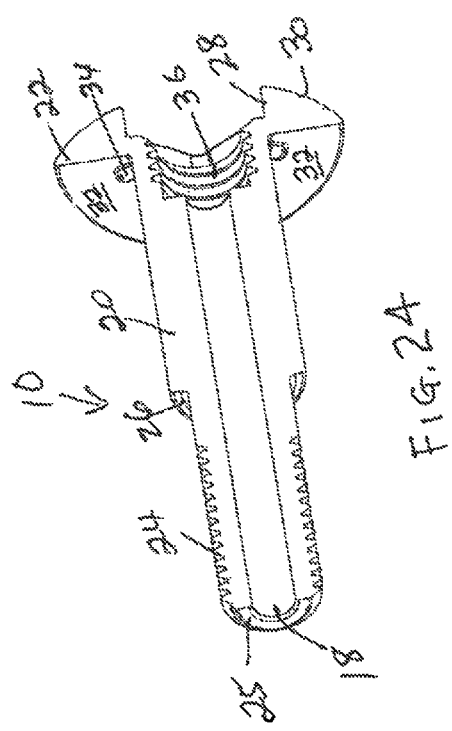
FIG. 24 is a sectional view of the other member shown in FIG. 23 taken along the mid-plane.

An expandable spinal prosthesis for insertion into an annulotomy hole created laterally in a spinal disc between two abutting vertebrae is shown in FIGS. 1-10. As shown, the novel spinal prosthesis device is in repose or at rest condition. FIGS. 17-19 show the novel spinal prosthesis device expanded to distract intentionally the abutting vertebrae. Structurally, the prosthesis consists of a two mating load bearing members, a first member 10 as shown in FIGS. 8-10 and a second member 12 as shown in FIGS. 4-7. The first member 10 consists of a shaft 20 having a through hole 18, an end cap 22 on one end 23 and a thread 24 on its other end 25. The diameter of the threaded portion 24 is reduced or less than the diameter of the shaft 20, and a shoulder 26 is defined therebetween. The end cap 22 has a hexagonal recess 28 formed in its convex end face 30, and a deeper threaded recess 36. An annular array of projections 34 are formed on the inner face 32 of end cap 22. The second member 12 consists of an end cap 40 fixed to a hollow tube 42 composed of spaced rings 44 and 46 interconnected by longitudinally extending bands 48 peripherally spaced around the tube 42. The end face 50 of the ring 46 is open and is provided with a plurality of spaced cutouts 52 that are shaped to mate with projections 34. The shape and design of the cutouts 52 and the projections 34 is such that they will hold the two members fixed together up to a preselected torque, beyond which the members will relatively rotate one with respect to the other. The inner diameter of tube 42 is sized to be received over shaft 20. The end cap 40 defines a threaded recess 54 to mate with threaded portion 24 of the first member 10. The two members 10 and 12 are assembled by sliding the end 25 of shaft 20 inside tube 42 from the open end of tube 42 where the cutouts 52 are. The threaded portion 24 is mated with the threads in recess 54. The projections 34 on end cap 22 are mated with the cutouts 52. The end cap 40 has a convex exterior, radially outer surface 56 and a flat exterior, radially inner surface 58. A raised annular projection 60 having a hexagonal perimeter extends from exterior surface 58. When members 10 and 12 are assembled they are covered by a transparent resilient membrane 66 composed of a suitable biomaterial.

Figure 11:
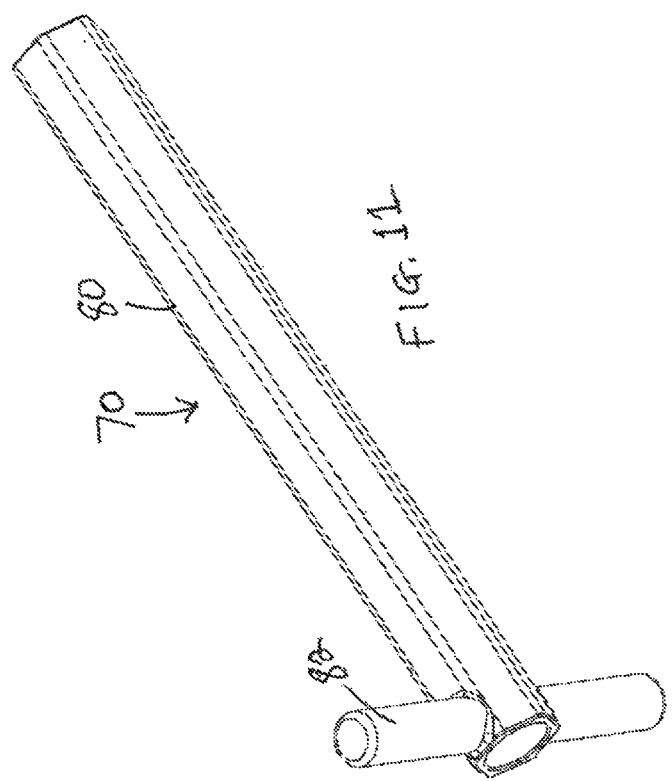
FIG. 11 is a perspective view of a hex tool for implanting one member of the prosthesis.
Figure 12:
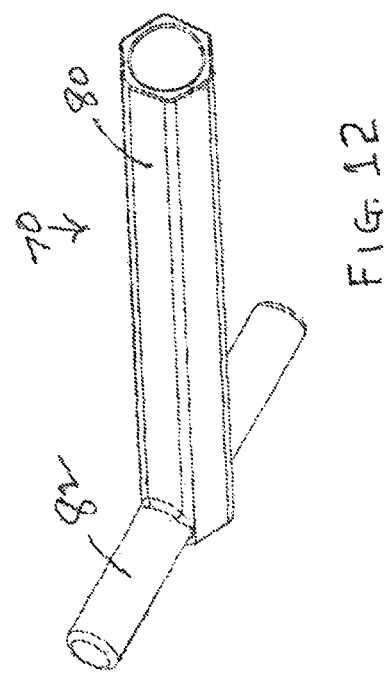
FIG. 12 is another perspective view of the hex tool of FIG. 11.
Figure 13:
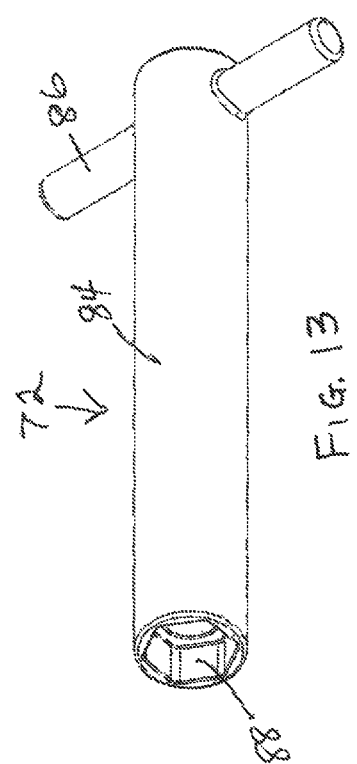
FIG. 13 is a perspective view of a hex tool for implanting the other member of the prosthesis.
Figure 14:
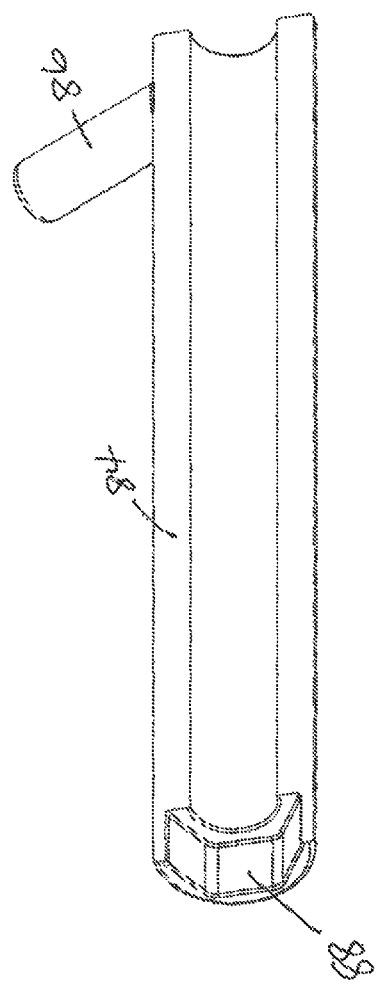
FIG. 14 is a sectional view of the hex tool shown in FIG. 13 taken along its mid-plane.
Figure 15:
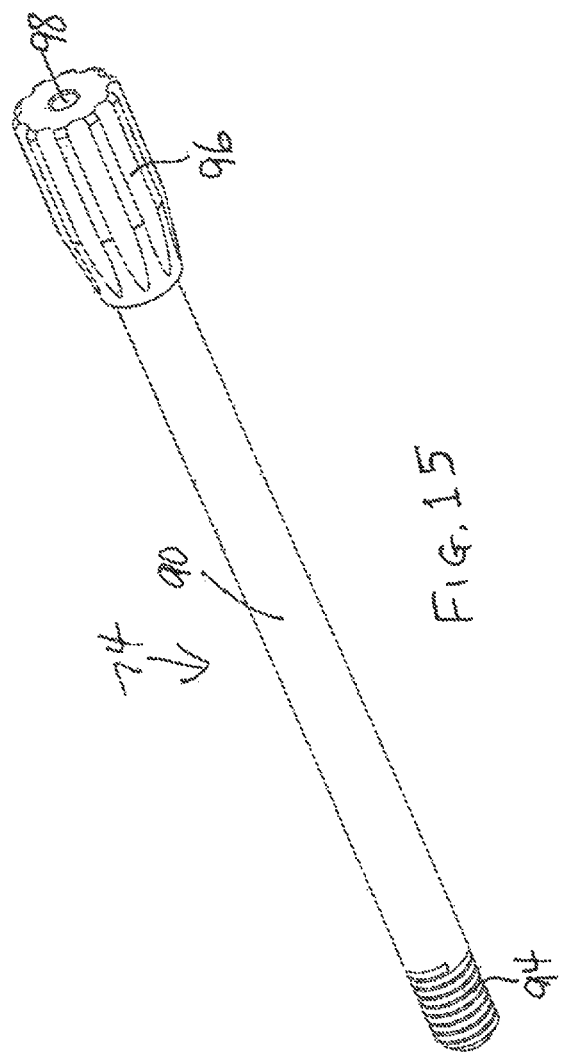
FIGS. 15 and 16 are perspective views of a stabilizing tool for implanting and explanting the prosthesis.
Figure 16:
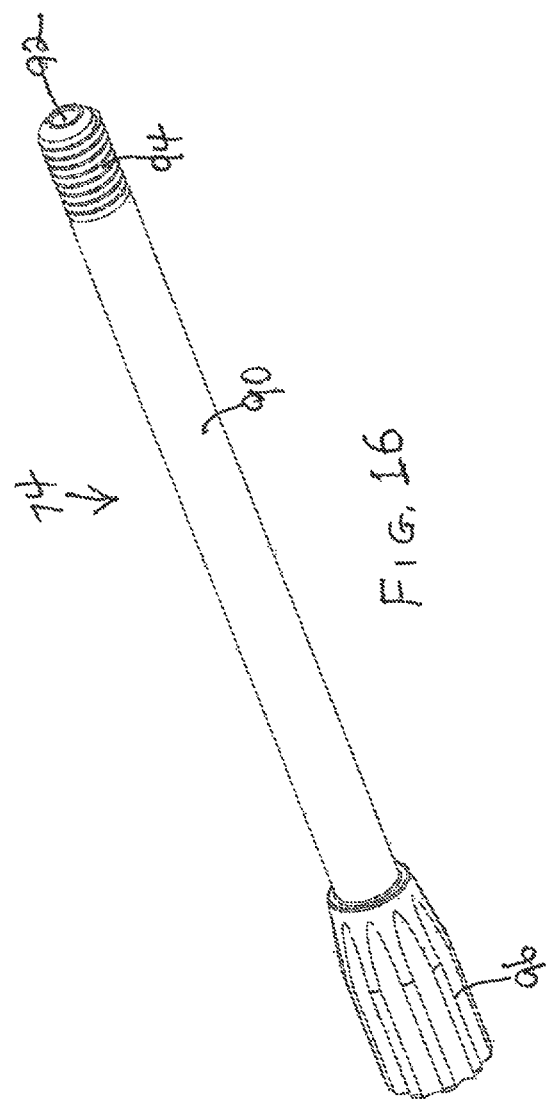

The implant tools are shown in FIGS. 11-16 and consist of an implant tool 70 for member 10, an implant tool 72 for member 12, and an implant tool 74 used for both members 10 and 12. The tool 70 is shown in FIGS. 11 and 12 and consists of a hollow, open-ended tube 80 the exterior shape of which is hexagonal. The end of tube 80 is sized to fit into the recess 28 of member 10. Handles 82 are fixed to one end of the tube 80 in a manner not to intrude into the interior. FIGS. 13 and 14 show implant tool 72 for engaging the hexagonal projection 60 of member 12. Tool 72 consists of a hollow, open-ended tube 84 having non-intrusive handles 86 fixed on one end and a hexagonal cutout 88 in its other end for engaging the hexagonal projection 60. Stabilizing tool 74 is shown in FIGS. 15 and 16 and consists of a shaft 90 having a through-hole 92 with threading 94 at one end and a knurled knob 96 with a through hole 98 aligned with through hole 92 at the other end. The threading 94 is sized to mate with the threads 36 in member 10 and with threads 54 in member 12.

Referring back to FIGS. 1-3, the prosthesis as described is shown coupled to implant tools. The bands 48 are in their repose or at rest condition. The prosthesis is implanted according to the following. To Implant:

1. Length and diameter of prosthesis is chosen pre-operatively based on diagnostic imaging measurements such that the diameter of the prosthesis is slightly greater than the height of the disc.
2. A patient is placed prone on the operating table.
3. A tube retractor or similar retractor is placed from the right side to bear upon and allow visualization of the right lateral part of the spinal disc.
4. A second tube retractor or similar retractor is then placed from the left side to bear upon and allow visualization of the left lateral aspect of the same disc.
5. A wire 100 is passed through-and-through the disc from one side to the other.
6. A tract is therefore created through the disc and is controllable from both sides.
7. The tract is dilated with a series of dilators—the dilators are passed down the wire 100 from either or both sides and then removed.
8. From the right side, the first "half" of a main load-bearing center piece, member 10, is placed, with the right end cap 22 attached using implant tools.
9. From the left side, the second "half" of the load-bearing center piece, member 12, greater diameter than the right "half," with end cap 40 is placed using implant tools, mating with the first half.
10. Tools 70 and 72 are then turned in opposite directions, relatively moving the end caps 22 and 40 closer together thereby expanding the prosthesis within the disc so it is transformed to the shape shown in FIG. 17.
11. The tools and wire are now removed leaving the prosthesis in place.

Although the prosthesis is shown with two flanged end caps, it is possible for the prosthesis to have only one flanged end cap 40 and end cap 102 without a flange or both end caps 102 and 104 without flanges, see FIGS. 18 and 19, respectively. End caps 102 and 104 are structurally like end caps 22 and 40 but without flanges.

As shown in FIGS. 20-24, the expansible prosthesis has been replaced by a prosthesis similar in structure except that a member 12a replaces member 12 with member 12a being composed of an end cap 40a fixed to an open-ended, unbroken, hollow, cylindrical tube 42a. The tube diameter is slightly greater than the height of the disc into which it will be placed. The open-end face 50a of tube 42a is provided with a plurality of spaced cutouts 52a that are shaped to mate with projections 34 of member 10. The end cap 40a has a convex exterior, radially outer surface 56a and a flat exterior, radially inner surface 58a. A raised annular projection 60a having a hexagonal perimeter extends from exterior surface 58a. The inner diameter of tube 42a is sized to be received over shaft 20. The end cap 40a defines a threaded recess 54a to mate with threaded portion 24 of the first member 10. For clarity member 10 is shown again in FIGS. 23-24.

Figure 25:
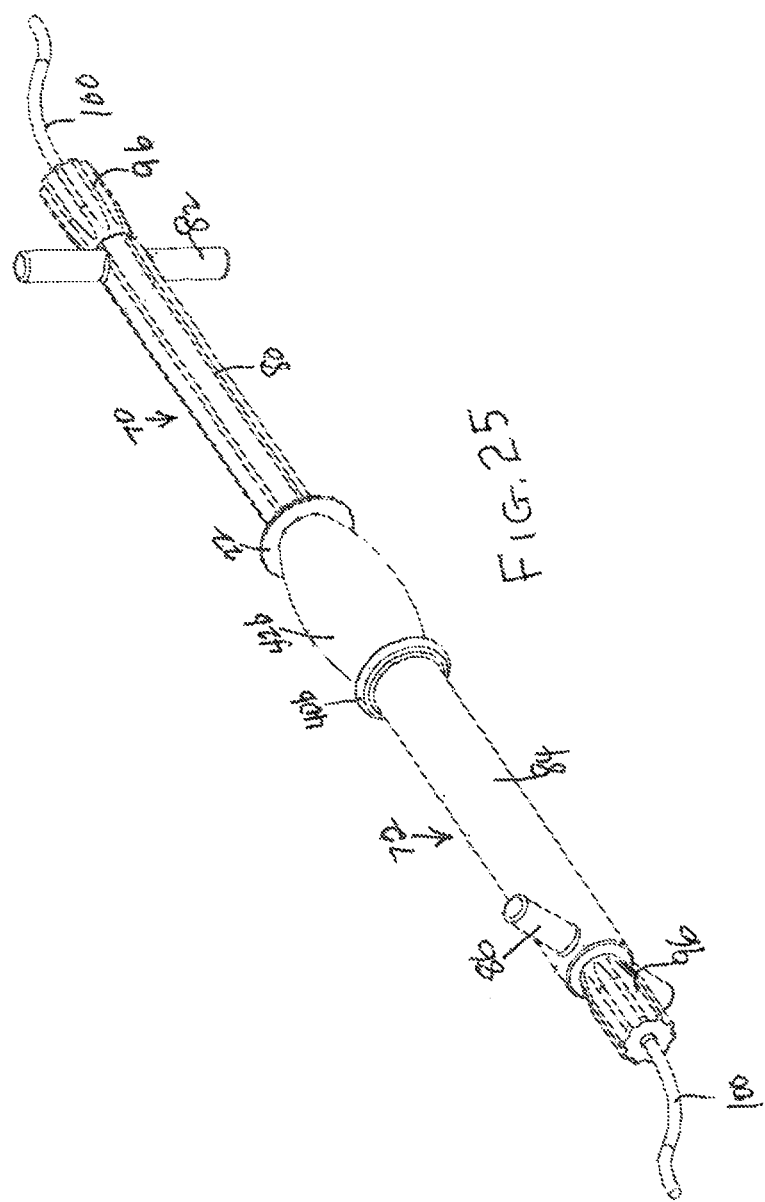
FIG. 25 is perspective view of a prolate spheroid prosthesis with tool coupled, the prosthesis having flanged end caps.
Figure 26:
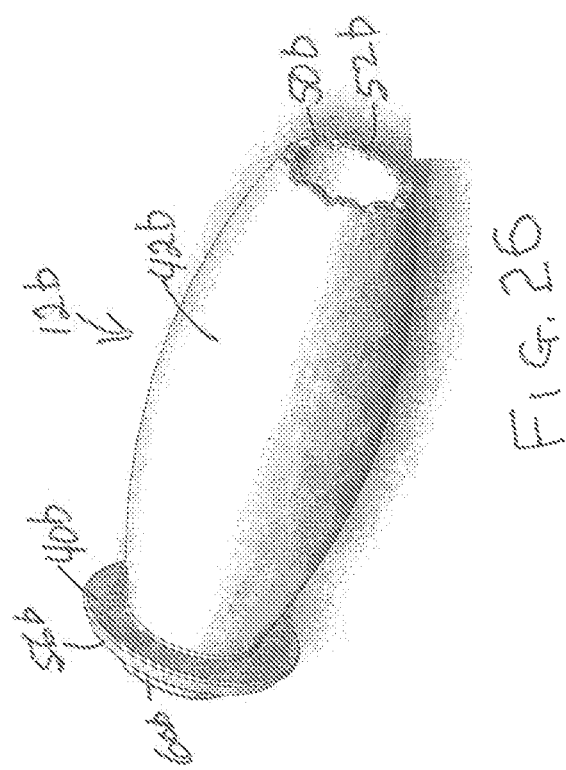
FIG. 26 is a perspective view of one member of the prosthesis shown in FIG. 25.

As shown in FIGS. 25-27, the expansible prosthesis has been replaced by a prosthesis similar in structure except that a member 12b replaces member 12 with member 12b being composed of an end cap 40b fixed to an open-ended, unbroken, hollow, prolate spheroid tube 42b. The maximal diameter of the prolate spheroid that of its midpoint, is slightly greater than the height of the disc into which it will be placed. The open-end face 50b of tube 42b is provided with a plurality of spaced cutouts 52b that are shaped to mate with projections 34 of member 10. The end cap 40b has a convex exterior, radially outer surface 56b and a flat exterior, radially inner surface 58b. A raised annular projection 60b having a hexagonal perimeter extends from exterior surface 58b. The inner diameter of tube 42b is sized to be received over shaft 20. The end cap 40b defines a threaded recess 54b to mate with threaded portion 24 of the first member 10, which is unchanged.

Both structures described in FIGS. 20-24 and 25-27 can use end caps that are flanged or not as described above. Also, it is possible to use a conical structure for member 12. To implant the structures shown in these figures and described above, including conical structures, the prostheses are coupled to implant tools in the manner described and are implanted according to the following. To Implant:
1. Length and diameter of prosthesis is chosen pre-operatively based diagnostic imaging measurements such that the maximal diameter of the prosthesis is slightly greater than the height of the disc into which it will be placed.
2. A patient is placed prone on the operating table.
3. A tube retractor or similar retractor is placed from the right side to bear upon and allow visualization of the right lateral part of the spinal disc.
4. A second tube retractor or similar retractor is then placed from the left side to bear upon and allow visualization of the left lateral aspect of the same disc.
5. A wire 100 is passed through-and-through the disc from one side to the other.
6. A tract is therefore created through the disc and is controllable from both sides.
7. The tract is dilated with a series of dilators—the dilators are passed down the wire from either or both sides and then removed.
8. From the right side, the first "half" of a main load-bearing center piece, member 10, is placed using implant tools, with the right end cap 22 attached.
9. From the left side, the second "half" of the load-bearing center piece, member 12a or 12b, greater diameter than the right "half," with end cap 40a or 40b, is placed using implant tools, mating with the first half.
10. The implant tools and wire 100 are now removed leaving the prosthesis in place.

To explant the prosthesis in either case the following procedure is followed.
1. Tube retractors or similar retractors are placed against both right and left lateral aspects of the intervertebral disc in which the prosthesis is implanted.
2. Tools 70, 72 and 74 are replaced into opening 28, projection 60 and openings 54 and 26, respectively.
3. Tools 70 and 72 are rotated in opposite directions thereby un-mating the two halves of the prosthesis.
4. Both halves are now pulled apart and out of the body.

Although the invention has been described in specific embodiments, changes and modifications will be evident to persons skilled in the art, which do not depart from the spirit and scope of the teachings herein. Such changes are deemed to fall within the purview of the invention as claimed.

What is claimed is:

1. An elongated spinal prosthesis composed of first and second parts each having a proximal end and a distal end, said first and second parts configured to be inserted bilaterally into opposite ends of a through-and-through annulotomy hole created laterally in a spinal disc between two abutting vertebrae;
said first part composed of an elongated shaft having a proximal end and a distal end for insertion into one end of the through-and-through annulotomy hole;
said elongated shaft defining a central axial hole therethrough;
a first end cap fixed to said elongated shaft at its proximal end;
said first end cap (i) defining a non-circular recess to receive a driver, (ii) a through bore and (iii) a first portion of a two portion disengageable engagement structure on the distal side of said first end cap;
the distal end of said elongated shaft defining first threading; and
the second part composed of a hollow elongated tube having a proximal end and a distal end for insertion into the other end of the through-and-through annulotomy hole;
said hollow elongated tube being of greater diameter than the elongated shaft and having a second end cap defining a non-circular recess for receiving a driver fixed to said hollow elongated tube at its proximal end;
the distal end of said hollow elongated tube being open-ended and defining a second portion of the two portion disengageable engagement structure to coact with said first portion of the two portion disengageable engagement structure; and
the proximal end of said hollow elongated tube defining second threading to mesh with the first threading;
whereby said two parts, when inserted into the through-and-through annulotomy hole will telescope together and the first and second threading will mesh and the two portions of the two portion disengageable engagement structure will engage to hold the first end cap and the distal end of the hollow elongated tube together up to a preselected torque beyond which the first end cap and the hollow elongated tube will rotate relative to each other,
wherein the hollow elongated tube includes a plurality of resilient bands peripherally spaced and extending longitudinally between the first and second end caps, said bands being outwardly bendable without exceeding their elastic limit below said preselected torque.

2. The spinal prosthesis according to claim 1 wherein the hollow elongated tube has a shape of one of cylindrical, prolate spheroid and conical.

3. The spinal prosthesis according to claim 1 wherein relative rotation of the first and second parts in one direction will cause the first and second end caps to move toward each other to cause the resilient bands to bend outwardly to expand the prosthesis and in an opposite direction will cause the first and second end caps to move apart to cause the resilient bands to become unbent and collapse the prosthesis.

4. The spinal prosthesis according to claim 1 wherein the two parts collectively define a longitudinal through hole through the prosthesis to enable a wire to pass through the prosthesis.

5. The spinal prosthesis according to claim 1 wherein the first and second end caps are flanged to enable said first end cap and said second end cap to engage the two abutting vertebrae to hold the prosthesis in position when inserted into the through-and-through annulotomy hole.

6. The spinal prosthesis according to claim 1 wherein the two portions of the two portion disengageable engagement structure comprise cutouts on one of the first end cap and hollow elongated tube and projections on the other of the first end cap and hollow elongated tube.

7. The spinal prosthesis according to claim 1 wherein the diameter of said elongated shaft at its proximal end is greater than the diameter at its distal end.

8. A method for implanting a disc prosthesis in a disc space between two abutting vertebrae, the prosthesis composed of two components, each component consisting of a main load-bearing body portion and an end cap fixed to one end of the main load-bearing body portion wherein the main load-bearing body portions of the two components are of different diameter to enable telescoping together, the two components of said disc prosthesis including distinct portions of a two portion disengageable engagement structure that are engageable to hold the two components together up to a preselected torque beyond which the two components will rotate relative to each other, comprising the steps of:
 a. forming a through-and-through tract in a disc space between two abutting vertebrae;
 b. inserting a wire into the through-and-through tract in the disc space so that the wire projects out of opposite ends of the through-and-through tract;
 c. mounting the two components on the wire projecting out of opposite ends of the through-and-through tract by inserting the projecting wire into and through through-holes in the two components;
 d. introducing bilaterally spinally toward one another the wire-mounted two components into the through-and-through tract; and
 e. coupling the components together between the two abutting vertebrae by telescoping the two components together until distinct portions of the two portion disengageable engagement structure become engaged to hold the two components together,
  wherein the greater diameter main load-bearing component defines peripherally spaced, longitudinally extending resilient bands having a preselected elastic limit, and including the further step f. of manipulating the two end caps of the coupled main load-bearing components in one direction to cause the resilient bands to bend outwardly without exceeding the preselected elastic limit.

9. The method according to claim 8 wherein the greater diameter main load-bearing body portion of the prosthesis has one of a conical, cylindrical and prolate spheroid shape.

10. The method of claim 8 including the further steps of g. manipulating the two end caps of the coupled main load-bearing components in an opposite direction to cause the resilient bands to collapse inwardly; and h. decoupling the two components and withdrawing them from the through-and-through tract to explant the prosthesis.

* * * * *